US007865004B2

(12) United States Patent
Moriya

(10) Patent No.: US 7,865,004 B2
(45) Date of Patent: Jan. 4, 2011

(54) SYSTEM, METHOD, AND PROGRAM FOR MEDICAL IMAGE INTERPRETATION SUPPORT

(75) Inventor: Yoshiyuki Moriya, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 693 days.

(21) Appl. No.: 11/874,360

(22) Filed: Oct. 18, 2007

(65) Prior Publication Data

US 2008/0095418 A1    Apr. 24, 2008

(30) Foreign Application Priority Data

Oct. 18, 2006    (JP)    ............................. 2006-283534

(51) Int. Cl.
*G06K 9/00*    (2006.01)
*A61B 5/00*    (2006.01)
(52) U.S. Cl. .......................................... 382/128; 705/3
(58) Field of Classification Search ................ 382/128, 382/129, 130, 131, 132, 133, 134, 190, 209, 382/305; 600/407, 41, 443; 128/920, 922; 705/3; 707/999.006
See application file for complete search history.

(56) References Cited

U.S. PATENT DOCUMENTS

| 6,584,223 | B1 * | 6/2003 | Shiiyama ..................... 382/173 |
| 6,901,156 | B2 * | 5/2005 | Giger et al. .................. 382/128 |
| 6,925,199 | B2 * | 8/2005 | Murao .......................... 382/131 |
| 7,200,612 | B2 * | 4/2007 | Brady et al. ........................ 1/1 |
| 2003/0013951 | A1 | 1/2003 | Stefanescu et al. |

* cited by examiner

*Primary Examiner*—Abolfazl Tabatabai
(74) *Attorney, Agent, or Firm*—Sughrue Mion, PLLC

(57) ABSTRACT

The number of similar case images to be displayed is changed according to the number of times and progress of imaging diagnosis. First examination judgment means is added to a medical image interpretation support system comprising storage means for storing image data sets obtained by imaging subjects, similar case image search means for extracting similar case image data sets having a characteristic similar to an interpretation target image from the image data sets, and display control means for controlling display of the interpretation target image and the similar case images. The display control means controls the display so as to display a larger number of the similar case images together with the interpretation target image in the case where the interpretation target image has been judged to be a first examination image than in the otherwise case.

8 Claims, 9 Drawing Sheets

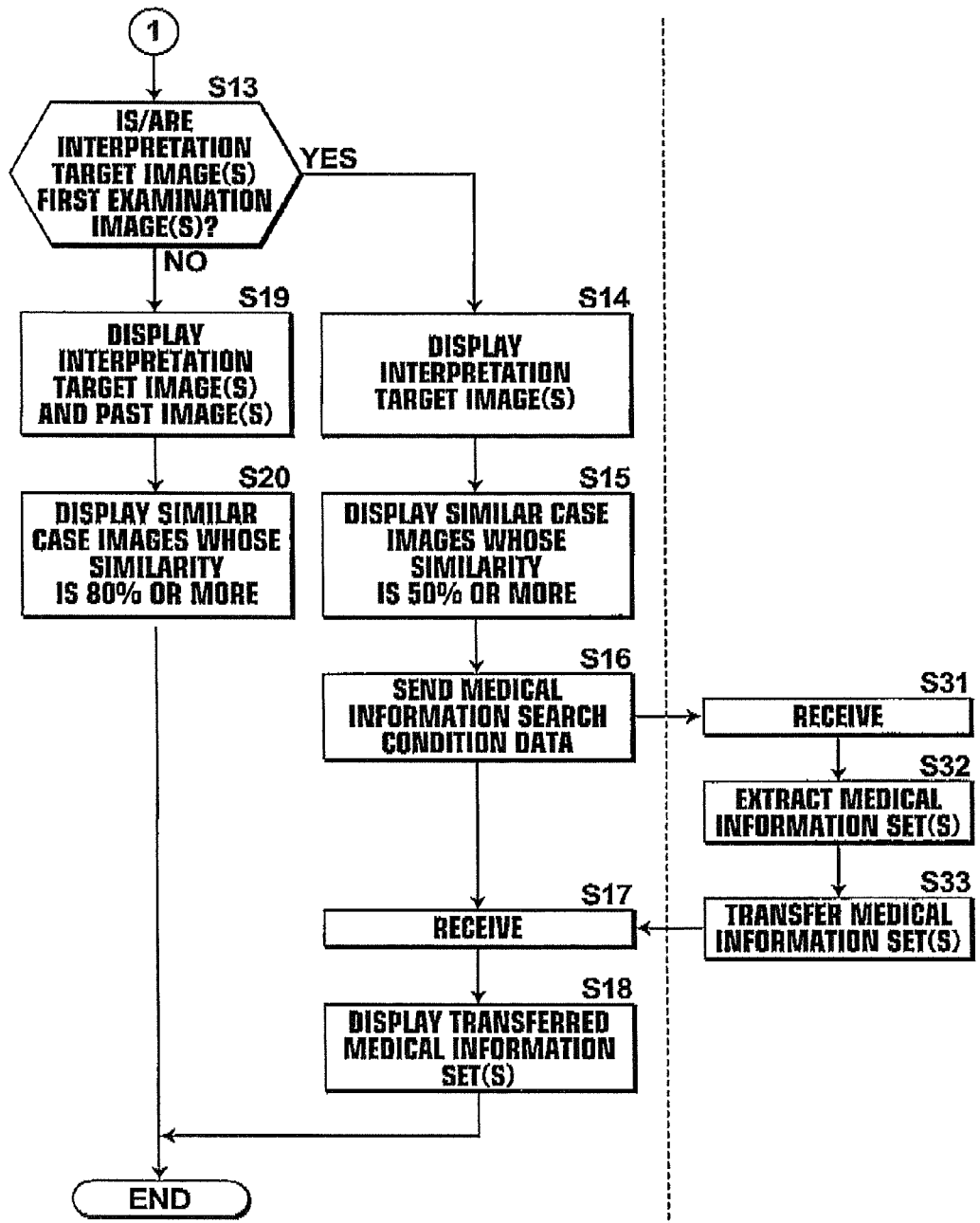

SYSTEM, METHOD, AND PROGRAM FOR MEDICAL IMAGE INTERPRETATION SUPPORT

BACKGROUND OF THE INVENTION

1. Field of the Invention

The present invention relates to a medical image interpretation support system and a medical image interpretation support method for supporting interpretation of a medical image, and to a program therefor.

2. Description of the Related Art

Progresses have been made in development of medical image interpretation support systems wherein medical images obtained by various types of modalities such as CT (Computed Tomography) and MR (Magnetic Resonance) are stored in databases and extracted from the databases upon necessity for display on monitors or the like. By using such a medical image interpretation support system, not only a medical image obtained in a recent examination but also a medical image obtained in the past and extracted from a database can be displayed on a monitor.

In a medical image interpretation support system having a similar case search function to extract similar case images that are similar to a case of a patient from a database, a physician as an image interpreter can use the similar case images displayed on a monitor as reference images. Such systems having the similar case search function have been described in U.S. Patent Application Publication No. 20030013951 and in U.S. Pat. No. 6,925,199.

In the systems described in U.S. Patent Application Publication No. 20030013951 and in U.S. Pat. No. 6,925,199, similar case images that are similar to an image of a patient as a subject are displayed on a monitor, regardless of whether the patient's image as a target of interpretation (an interpretation target image) for a physician is an image obtained in a first examination of the patient (a first examination image) or an image obtained in a later examination (in a follow-up examination). However, in reality, the content and quantity of similar case images as references for diagnosis of a first examination image are different from those as references for diagnosis of an image obtained in a follow-up examination. Therefore, conventional systems having the similar case search function are inconvenient, since the systems cannot efficiently search for and display similar case images according to the number of times of imaging diagnosis.

SUMMARY OF THE INVENTION

The present invention has been conceived in consideration of the above circumstances, and an object of the present invention is to provide a system, a method, and a program for medical image interpretation support that enable to change the number of similar case images to be displayed according to whether an interpretation target image is a first examination image.

In order to solve the problem described above, a medical image interpretation support system of the present invention comprises:

storage means for storing image data sets obtained by imaging patients;

similar case search means for extracting similar case image data sets representing similar case images having a characteristic similar to an interpretation target image or interpretation target images from the image data sets stored in the storage means; and display control means for controlling display of the interpretation target image or images and the similar case images on a monitor or monitors. The medical image interpretation support system of the present invention is characterized by that the system further comprises first examination judgment means for judging whether the interpretation target image or images is/are a first examination image/first examination images. In the case where the first examination judgment means has judged that the interpretation target image or images is/are a first examination image or first examination images, the display control means controls the display in such a manner that the number of the similar case images displayed together with the interpretation target image or images is larger than the number of the similar case images displayed together with the interpretation target image or images in the case where the first examination judgment means has judged that the interpretation target image or images is/are not a first examination image or first examination images.

Here, the "first examination image/first examination images" refer to an image or images which are obtained upon initial consultation by a patient.

The medical image interpretation support system of the present invention may further comprise medical information search means for extracting medical information. In the case where the first examination judgment means has judged that the interpretation target image or images is/are a first examination image or first examination images, the display control means controls the display to further display the medical information extracted by the medical information search means.

The medical image interpretation support system of the present invention may further comprise past image search means for extracting at least one past image data set representing a past image or past images obtained in the past regarding the same patient as the interpretation target image or images from the image data sets stored in the storage means. In the case where the first examination judgment means has judged that the interpretation target image or images is/are not a first examination image or first examination images, the display control means controls the display to further display the past image or images extracted by the past image search means.

The first examination judgment means may judge that the interpretation target image or images is/are a first examination image or first examination images in the case where the past image search means cannot extract the past image data set or sets.

The past image search means may extract the past image data set or sets of the patient including the same body part as the interpretation target image or images.

The medical image interpretation support system of the present invention may further comprise electronic chart storage means for storing electronic charts including history information of examinations involving imaging. In this case, the first examination judgment means may judge whether the interpretation target image or images is/are a first examination image/first examination images by referring to the history information included in a corresponding one of the electronic charts to the patient of the interpretation target image or images stored in the electronic chart storage means.

A medical image interpretation support method of the present invention comprises the steps of:

extracting similar case image data sets representing similar case images having a characteristic similar to an interpretation target image or interpretation target images from image data sets obtained by imaging patients and stored in storage means; and displaying the interpretation target image or images and the similar case images on a monitor or monitors. The step of displaying comprises the steps of:

judging whether the interpretation target image or images is/are a first examination image/first examination images; and displaying the similar case images together with the interpretation target image or images in such a manner that the number of the similar case images displayed together with the interpretation target image or images in the case where the interpretation target image or images has/have been judged to be a first examination image or first examination images is larger than the number of the similar case images displayed together with the interpretation target image or images in the case where the interpretation target image or images has/have been judged to be not a first examination image or first examination images in the step of judging.

A recording medium storing a medical image interpretation support program of the present invention causes a computer to execute procedures of first examination judgment and display control. The computer comprises a medical image interpretation support system including:

storage means for storing image data sets obtained by imaging patients;

similar case search means for extracting similar case image data sets representing similar case images having a characteristic similar to an interpretation target image or interpretation target images from the image data sets stored in the storage means; and display control means for controlling display of the interpretation target image or images and the similar case images on a monitor or monitors. The computer has the display control means and is caused to execute:

the first examination judgment procedure for judging whether the interpretation target image or images is/are a first examination image/first examination images; and the display control procedure for controlling the display in such a manner that the number of the similar case images displayed together with the interpretation target image or images in the case where the interpretation target image or images has/have been judged to be a first examination image or first examination images in the first examination judgment procedure is larger than the number of the similar case images displayed together with the interpretation target image or images in the case where the interpretation target image or images has/have been judged to be not a first examination image or first examination images in the first examination judgment procedure.

By displaying a larger number of the similar case images together with the interpretation target image or images in the case where the interpretation target image or images is/are a first examination image or first examination images than in the case where the interpretation target image or images is/are not a first examination image or first examination images, the similar case images can be displayed in accordance with the number and progress of examinations. Therefore, image information of appropriate content can be provided to an image interpreter.

BRIEF DESCRIPTION OF THE DRAWINGS

FIG. 6 is a flow chart showing procedures of the medical image interpretation support processing (part 2);

DESCRIPTION OF THE PREFERRED EMBODIMENT

Figure 1:
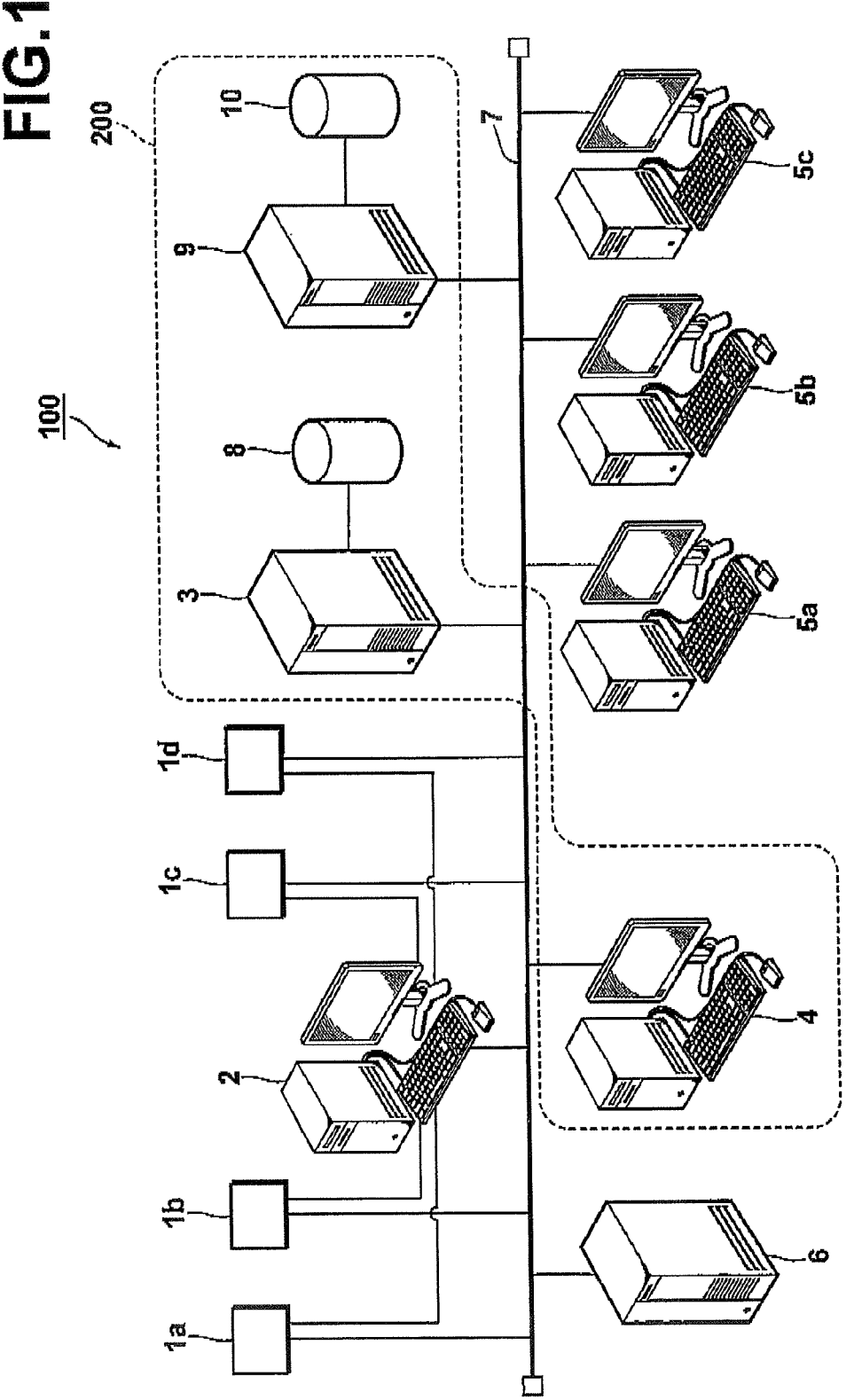
FIG. 1 is shows the configuration of a network system having a medical image interpretation support system.

Hereinafter, an embodiment of the present invention will be described with reference to the accompanying drawings. FIG. 1 shows an example of the configuration of a network system 100 having a medical image interpretation support system 200 of the present invention. The network system 100 is mainly for a hospital, or a clinic, or the like. The network system 100 comprises modalities 1a to 1d, a workstation 2 for image confirmation (hereinafter referred to as the image confirmation workstation 2), a server 3 having a medical image database (storage means) 8, a workstation 4 for imaging diagnosis (hereinafter referred to as the imaging diagnosis workstation 4), workstations 5a to 5c for referring to images (hereinafter referred to as the image reference workstations 5a to 5c), a radiology information system (RIS) 6, a server 9 having a medical information database 10, and a hospital information system (HIS) and the like that are not shown, all of which are connected in a communicable state via a network 7. The medical image interpretation support system 200 comprising the server 3, the medical image database 8, the imaging diagnosis workstation 4, the server 9, and the medical information database 10 is the embodiment of the medical image interpretation support system of the present invention.

The modalities 1a to 1d and the image confirmation workstation 2 are installed in an imaging room of the hospital or the like, and usually operated by a technician who is dedicated to imaging. The modalities 1a to 1d include modalities of CT, MR, ultrasonography or the like that directly generate image data sets from data obtained by imaging and modalities such as CR (Computed Radiography) and mammography that generate image data sets through readout of images obtained by imaging from recording media such as films. A reading apparatus (not shown) for reading the images from the recording media is connected to the network 7 for the latter type of modalities. The modalities 1a to 1d in this embodiment conform to the DICOM standard, and each of the modalities 1a to 1d outputs image data sets added with accompanying information defined by the DICOM standard as image information sets. Hereinafter, the image information sets refer to information sets each comprising an image data set and the accompanying information.

The image confirmation workstation 2 comprises a processor, one or two high definition display(s), and input devices such as a keyboard and a mouse. A software program that provides various functions necessary for image confirmation is installed in the processor. The image confirmation workstation 2 has a communication function to receive the image information sets according to the DICOM standard from the modalities 1a to 1d and to transfer the image information sets having been confirmed to the server 3.

The server 3 has a function of filing system for storing the image information sets transferred from the image confirmation workstation 2 in the medical image database 8 and a function as an image server that provides the filed image information sets in a referable state in response to requests of the imaging diagnosis workstation 4 and the image reference workstations 5a to 5c. The medical image database 8 may be a hard disk connected directly to the server 3, or a network attached storage (NAS) or a storage area network (SAN) connected to the network 7. In any case, it is preferable for the medical image database 8 to comprise RAID (Redundant Arrays of Inexpensive Disks), in order to improve fault resiliency.

A physician in a radiology ward (hereinafter referred to as the radiologist) uses the imaging diagnosis workstation 4 and the radiology information system 6. The imaging diagnosis workstation 4 is used by the radiologist to interpret an image, and comprises a processor, one or two high definition display(s), a keyboard, a mouse, and the like. The processor has various kinds of programs installed therein that provide functions to support diagnosis by the radiologist, such as a function to display a part that seems to be a lesion in an image with emphasis by automatic detection of the part and a function to support generation of a diagnosis report. The imaging diagnosis workstation 4 also has a function to obtain the image information sets according to the DICOM standard by accessing the server 3 and a function to transfer diagnosis information including the diagnosis report to the server 3.

The radiology information system 6 provides various functions to support coordination between the radiologist and the technician and to improve efficiency of examinations. The radiology information system 6 comprises one or more computer(s). The radiology information system 6 also has a function to assign one of the modalities used for imaging based on examination order information input by a physician of each ward or by the radiologist. The examination order information refers to information including patient code, name of patient, examination code, name of examination, date of examination, and the like. The examination order information is transferred to the corresponding modality or to the image confirmation workstation 2 according to this function.

The modality or the image confirmation workstation 2 relates the transferred examination order information to an image data set having been generated. As a method of relating, the examination order information may be added as it is to the image information set as a part of the accompanying information, or link information to the examination order information may be added to the image information set as a part of the accompanying information, for example. A data structure therefor is not specifically limited.

The image reference workstations 5a to 5c are respectively installed in wards, and a physician in each of the wards uses the corresponding workstation in order to refer to the image information sets stored in the server 3 and to the diagnosis reports generated by the radiologist. Like the imaging diagnosis workstation, each of the reference workstations 5a to 5c comprises a processor, a high definition display, and input devices such as a keyboard and a mouse. The processor has a software program installed therein for providing a function to refer to the information sets and the like stored in the server 3.

The server 9 has a function to extract medical information corresponding to a search condition sent from the imaging diagnosis workstation 4 by searching the medical information stored in the medical information database 10, and a function to transfer the extracted medical information to the imaging diagnosis workstation 4. For each disease, the medical information database 10 stores basic information, the content of medical information journal or academic paper or the like and past issues thereof, and so on.

The network 7 is a local area network that connects various kinds of apparatuses in the hospital or the like. In the case where a part of the image reference workstations is installed in another hospital or a clinic, for example, the network 7 connects local area networks by the Internet or a dedicated line. In either case, it is desirable for the network 7 to be an optical network or the like that can realize high-speed transfer of the image information sets.

In the system described above, when the examination order information is input to the radiology information system 6, the examination order information is transferred to the modality used for imaging and to the image confirmation workstation 2. The technician then carries out imaging of a subject. After the imaging, the image information set output from the modality is displayed on a screen of the image confirmation workstation 2, and the technician carries out image confirmation and quality adjustment thereof. The image information set after the confirmation and adjustment is transferred to the server 3 and filed as the image information set in the medical image database 8. The filed image information set is displayed on a screen of the imaging diagnosis workstation 4 upon request of the radiologist, and the radiologist carries out diagnosis. After the diagnosis, the diagnosis information including the generated diagnosis report is sent to the server 3, and filed in the medical image database 8 by being related to the image information set. All the filed image information sets can be displayed on a screen of any one of the workstations 5a to 5c upon request of a physician.

Figure 2:
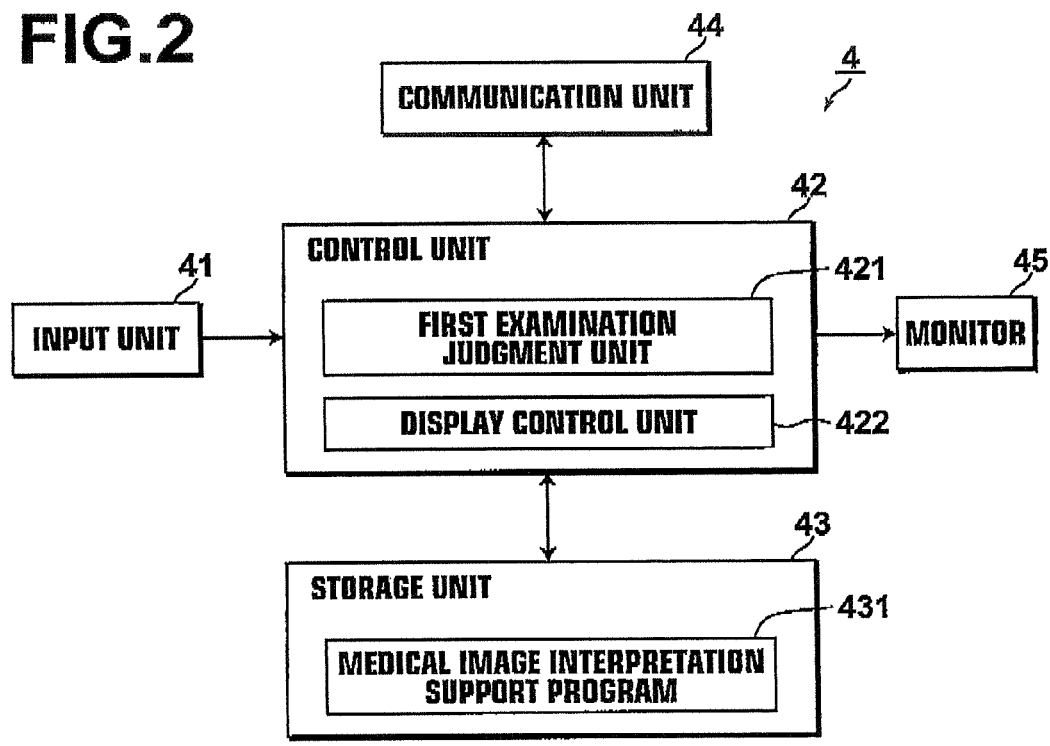
FIG. 2 shows the functional configuration of a workstation for imaging diagnosis.

FIG. 2 is a block diagram showing an example of the functional configuration of the imaging diagnosis workstation 4. The imaging diagnosis workstation 4 comprises an input unit 41, a control unit 42, a storage unit 43, a communication unit 44, and a monitor 45.

The input unit 41 comprises a keyboard and a pointing device such as a mouse or a touch panel. When being operated, the input unit 41 outputs an operation signal corresponding to the operation to the control unit 42. The radiologist inputs an identification number or the like (such as a file name or imaging number) of an interpretation target image or interpretation target images by use of the input unit 41.

The control unit (operation detection means) 42 carries out procedures based on a predetermined program according to the operation signal or an instruction signal input from the input unit 41 or the other functional units such as the communication unit 44, and carries out overall control of the functional units comprising the imaging diagnosis workstation 4, such as output of a control signal or data to the functional units and output of a display signal for display of a processing result on the monitor 45.

The control unit 42 also has a first examination judgment unit (first examination judgment means) 421 and a display control unit (display control means) 422. The first examination judgment unit 421 judges whether an image or images included in the image information set or sets as a target of image interpretation (hereinafter referred to as the interpretation target image information set or sets) transferred from the server 3 is a first examination image/first examination images. The first examination image or images refer(s) to a medical image or medical images of a patient as a subject obtained by imaging the patient for the first time. More specifically, the first examination judgment means 421 judges that the interpretation target image or images is/are a first examination image or first examination images in the case where no past image information set of the patient is sent from the server 3 together with the interpretation target image information set or sets. In the case where a past image information set or past image information sets has/have been transferred, the first examination judgment means 421 judges that the interpretation target image or images is/are not a first examination image or first examination images.

In the case where an electronic chart database (not shown in FIG. 1) that stores electronic chart information sets including diagnosis history and imaging history of patients is connected to the network 7, an electronic chart information set corresponding to the patient as the subject may be searched for and extracted from the electronic chart database so that judgment can be made as to whether the interpretation target image or images is/are a first examination image/first examination images with reference to the electronic chart information set. The electronic chart information sets include various kinds of history information related to diagnosis and personal information of patients, such as name of patient, address thereof, disease history, and medication history in addition to the diagnosis history and the imaging history.

In the case where the electronic chart information set is used to judge whether the interpretation target image or images is/are a first examination image/first examination images, the first examination judgment unit 421 requests transfer of the electronic chart information set of the patient as the subject of the interpretation target image or images from the electronic chart database via the communication unit 44, and reads the imaging history in the electronic chart information set having been transferred. In the case where the electronic chart information set does not include any history of imaging, the first examination judgment unit 421 judges that the interpretation target image or images is/are a first examination image or first examination images. Otherwise, the first examination judgment unit 421 judges that the interpretation target image or images is/are not a first examination image or first examination images. The first examination judgment unit 421 may judge that the interpretation target image or images is/are not a first examination image or first examination images in the case where the modality used for imaging and/or a body part having been imaged is/are the same, in addition to presence or absence of the imaging history.

The display control unit 422 generates display signals for displaying images, characters, operation buttons, and the like on the monitor 45, and outputs the signals to the monitor 45. The display control unit 422 also generates display signals for displaying similar case images and at least one medical information set together with the interpretation target image or images on the monitor 45 in the case where the interpretation target image or images is/are a first examination image or first examination images. In the case where the interpretation target image or images is/are not a first examination image or first examination images, the display control unit 422 generates display signals to display the interpretation target image or images, the similar case images, and at least one past image on the monitor 45. The similar case images refer to information including images that are pictorially similar to the interpretation target image, and the past image or images refer(s) to information including an image or images obtained in the past by imaging the patient who is the subject of the interpretation target image or images.

The display control unit 422 displays more similar case images in the case where the interpretation target image or images is/are a first examination image or first examination images than in the case where the interpretation target image or images is/are not a first examination image or first examination images. More specifically, in the case where the interpretation target image or images is/are a first examination image or first examination images, the display control unit 422 displays images whose similarity to the interpretation target image or images (the similarity refers to a value representing a degree of pictorial agreement with the interpretation target image or images) is 50% or more as the similar case images on the monitor 45 and otherwise displays images whose similarity to the interpretation target image or images is 80% or more as the similar case images on the monitor 45, for example. As has been described above, by displaying a larger number of the similar case images in the case where the interpretation target image or images is/are a first examination image or first examination images than in the case where the interpretation target image or images is/are not a first examination image or first examination images but an image or images obtained in a so-called follow-up examination, the similar case images can be displayed in accordance with the number and progress of examinations. Consequently, the image information sets of appropriate content can be efficiently provided to the radiologist.

In the embodiment described above, the similar case images whose similarity to the interpretation target image or images is 50% or more are displayed together with the interpretation target image or images if the interpretation target image or images is/are a first examination image or first examination images and the similar case images whose similarity is 80% or more are displayed together if otherwise. However, the values of similarity to the interpretation target image or images as display conditions are not necessarily limited to the values described above, as long as the similarity for the case where the interpretation target image or images is/are a first examination image or first examination images is lower than the similarity for the case where the interpretation target image or images is/are not a first examination image or first examination images. For example, similar case images whose similarity to the interpretation target image or images is 85% or more may be displayed if the interpretation target image or images is/are a first examination image or first examination images while similar case images whose similarity to the interpretation target image or images is 90% or more are displayed if otherwise. Alternatively, similar case images whose similarity to the interpretation target image or images is a predetermined value or more may be displayed only in the case where the interpretation target image or images is/are a first examination image or first examination images while no similar case images are displayed in the otherwise case.

The storage unit 43 is a recording medium wherein various kinds of programs and data are stored in advance, and comprises a magnetic or optical recording medium or a semiconductor memory, for example. The storage unit 43 stores a basic program (not shown) for causing the imaging diagnosis workstation 4 to operate, and a medical image interpretation support program 431 for controlling the monitor 45 to display the interpretation target image or images, the similar case images, the past image or images, and the like. The medical image interpretation support program 431 will be described later in detail. The storage unit 43 also stores a program for displaying on the monitor 45 an image part which seems to be a lesion by automatically detecting and emphasizing the part at the time of imaging diagnosis, a program for supporting generation of the diagnosis report, and the like, which are not shown in FIG. 2.

The communication unit 44 is an interface for sending and receiving data to and from the external equipment such as the server 3 and the server 9 connected to the network 7, and sends and receives data to and from the external equipment via the network 7 according to a control signal output from the control unit 42. More specifically, the communication unit 44 sends a signal to request transfer of an image information set to the server 3 according to the control signal output from the control unit 42. The communication unit 44 receives the image information set transferred from the server 3 in response to the signal, and outputs the image information set to the control unit 42. The communication unit 44 also sends a signal to request transfer of a medical information set to the server 9, and receives the medical information set transferred from the server 9 in response to the signal, to output the medical information set to the control unit 42. In addition, the communication unit 44 sends the diagnosis information including the diagnosis report generated by the radiologist by use of the input unit 41 and the like to the server 3.

The monitor 45 is a high definition display comprising an LCD (Liquid Crystal Display), or ELD (Electro-Luminescence Display), or the like. The monitor 45 displays images, characters, operation buttons, and the like according to the display signals output from the control unit 42.

Figure 3:
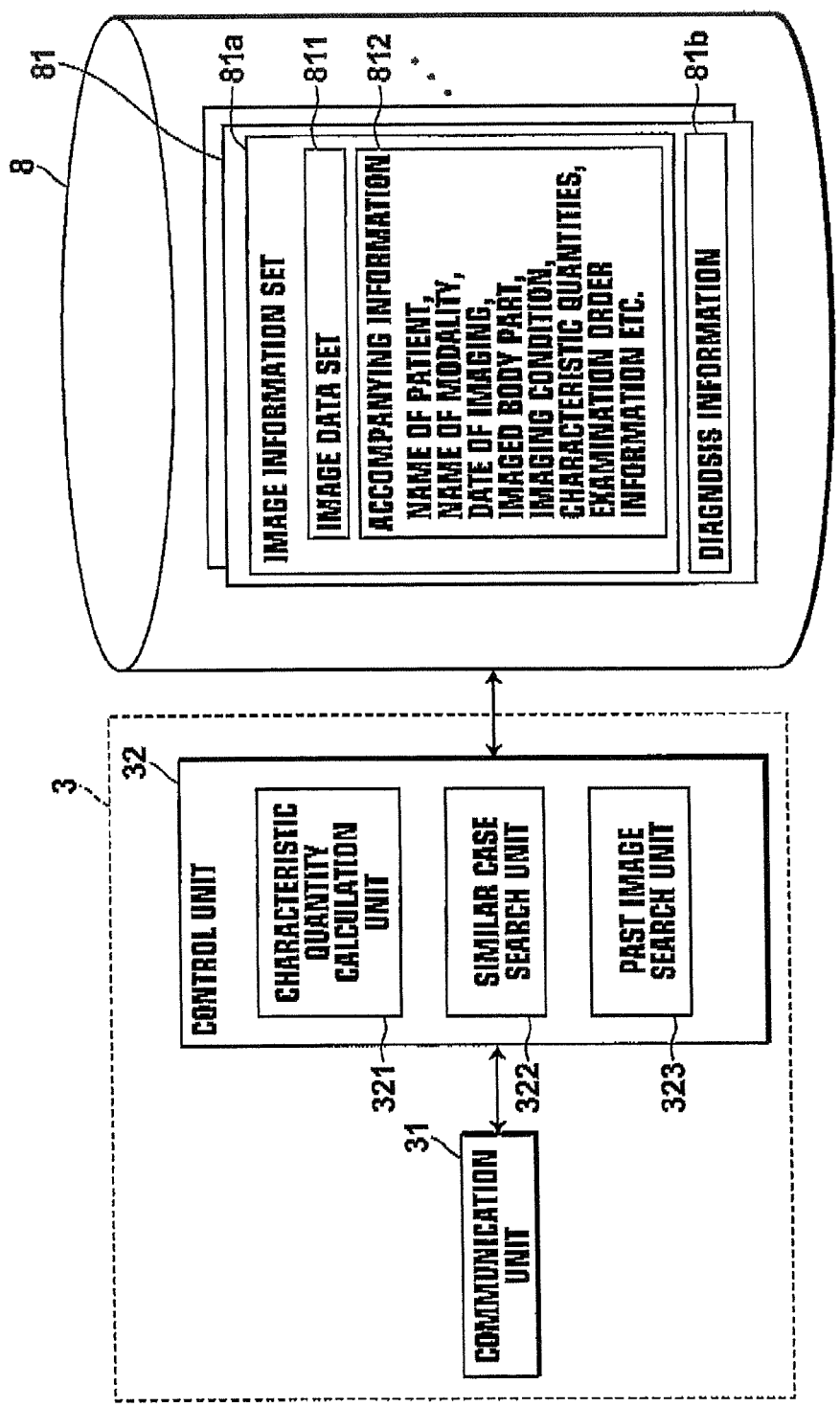
FIG. 3 shows the functional configuration of a server and a data structure of a medical image database.

FIG. 3 shows an example of the functional configuration of the server 3 and an example of a data structure in the medical image database 8. The data structure in the medical image database 8 will be described first. The medical image database 8 stores medical image information sets 81 each comprising an image information set 81*a* related to diagnosis information 81*b* including the diagnosis report. An image data set 811 is an image data set generated from an image obtained by any one of the modalities 1*a* to 1*d*. Accompanying information 812 is related to the image data set 811 and includes name of patient, name of modality used for imaging, date of imaging, imaged body part, imaging condition, and the examination order information as well as pictorial characteristic quantities and the like of at least one region of interest (hereinafter referred to as the region of interest which includes the case of regions of interest) that will be described later. The diagnosis information 81*b* includes the diagnosis report generated by the radiologist by use of the imaging diagnosis workstation 4.

The server 3 comprises a communication unit 31, a control unit 32, and the like. The communication unit 31 is an interface for sending and receiving data to and from the external equipment such as the image confirmation workstation 2, the imaging diagnosis workstation 4, the image reference workstations 5*a* to 5*c*, and the radiology information system 6 connected to the network 7. The communication unit 31 sends and receives data to and from the external equipment via the network 7 according to a control signal output from the control unit 32. More specifically, the communication unit 31 receives the image information sets from the image confirmation workstation 2, and receives the diagnosis information and the transfer request signal for an image information set from the imaging diagnosis workstation 4, and the like. The communication unit 31 also outputs the information, the signal, and the like to the control unit 32.

The control unit 32 carries out overall control of the functional units comprising the server 3, such as output of the control signal and data to the functional units, by executing procedures based on a predetermined program according to an instruction signal input from the other functional units such as the communication unit 31. The control unit 32 comprises a characteristic quantity calculation unit 321, a similar case search unit (similar case search means) 322, and a past image search unit (past image search means) 323. The characteristic quantity calculation unit 321 detects a lesion in the interpretation target image or images, and calculates the characteristic quantities in a region including the detected lesion. In the case where the radiologist has set the region including the lesion by use of the imaging diagnosis workstation 4 and the image information set or sets including information related to the region has been sent to the server 3, the characteristic quantity calculation unit 321 may calculate the characteristic quantities in the region having been set. The characteristic quantity calculation unit 321 includes the characteristic quantities in the accompanying information 812, and stores the information in the medical image database 8. Hereinafter, the region including the detected lesion or the region set by the radiologist to include the lesion is called the region of interest. The characteristic quantities in the region of interest can be calculated according to a known technique described in U.S. Pat. No. 6,925,199, for example.

The similar case search unit 322 searches the medical image database 8 for a portion of the medical image information sets 81 that includes images pictorially similar to the interpretation target image or images, and extracts the corresponding information sets as similar case image information sets. More specifically, the similarity is calculated by comparison of the characteristic quantities in the region of interest in the interpretation target image or images with the characteristic quantities included in the accompanying information 812 of the respective medical image information sets 81 stored in the medical image database 8, and the medical image information sets 81 whose similarity is a predetermined threshold value or larger are extracted.

It is preferable for the threshold value of the similarity to be a value of the similarity for display of the similar case images in the case of the interpretation target image or images being a first examination image/first examination images, or to be smaller than the similarity for the display. If the images whose similarity to the interpretation target image or images is 50% or more are displayed as the similar case images in the case where the interpretation target image or images is/are a first examination image or first examination images, it is preferable for the threshold value of the similarity to be 50% or less.

The characteristic quantities in the region of interest can be calculated according a known technique such as a method described in U.S. Pat. No. 6,925,199. The items such as the name of modality used for imaging, the imaged body part, and the imaging condition stored as the accompanying information 812 may be added as conditions besides the pictorial similarity to the interpretation target image or images. In this case, the similar case image information sets are extracted through calculation of the similarity by weighting the condition items if necessary.

The past image search unit 323 searches the medical image database 8 for a portion of the medical image information sets 81 that is related to the interpretation target image or images, based on the name of the patient included in the accompanying information of the interpretation target image information set or sets. The past image search unit 323 then extracts the corresponding image information set or sets 81. In addition to the name of the patient as a search condition, agreement of the modality used for imaging and agreement of the imaged body part may also be used as other search conditions.

Figure 4:
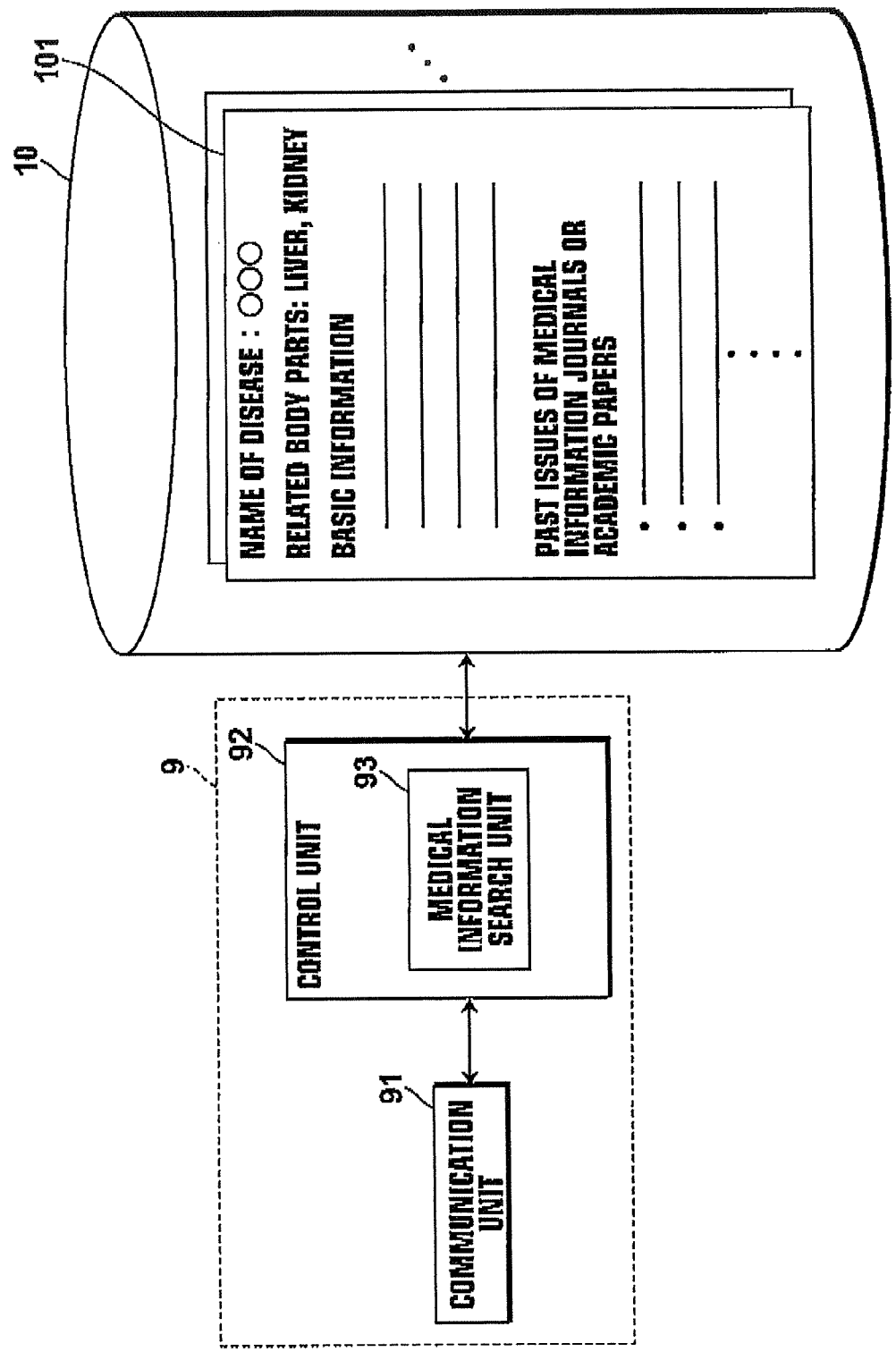
FIG. 4 shows the functional configuration of a server and a data structure of a medical information database.

FIG. 4 shows an example of the functional configuration of the server 9 and an example of a data structure of the medical information database 10. The structure of the medial information database 10 will be described first. The medical information database 10 stores medical information sets 101 for respective diseases. Each of the medical information sets 101 comprises header information representing the name of disease and a body part related to the disease, basic information related to the disease (a pathogenic mechanism, a cause, a symptom, a diagnosis method, a treatment method, and the like), and the content of journals of medical information or academic paper and past issues thereof, for example. The content of the header information, the basic information, the medical information journals and the past issues thereof, and the like are stored for each of the medical information sets 101 in a format readable by the server 9 and the control unit 42 of the imaging diagnosis workstation 4.

The server 9 comprises a communication unit 91, a control unit 92, and the like. The communication unit 91 is an interface for sending and receiving data to and from the external equipment such as the imaging diagnosis workstation 4 and the image reference workstations 5a to 5c connected to the network 7. The communication unit 91 sends and receives data to and from the external equipment via the network 7 according to a control signal output from the control unit 92. More specifically, the communication unit 91 receives medical information search condition data and the like sent from the imaging diagnosis workstation 4 and the image reference workstations 5a to 5c, and outputs the data to the control unit 92.

The communication unit 92 carries out overall control of the functional units comprising the server 9, such as output of a control signal and data to the functional units, by execution of procedures based on a predetermined program according to an instruction signal input from the functional units such as the communication unit 91.

The control unit 92 also has a medical information search unit (medical information search means) 93. The medical information search unit 93 searches the medical information database 10 for a portion of the medical information sets 101 that corresponds to the medical information search condition data received by the communication unit 91, and extracts the corresponding information set or sets. More specifically, in the case where the search condition data "liver" have been sent, the medical information search unit 93 extracts the medical information set or sets 101 whose item of related body parts is liver, and causes the communication unit 91 to transfer the extracted medical information set or sets 101.

Figure 5:
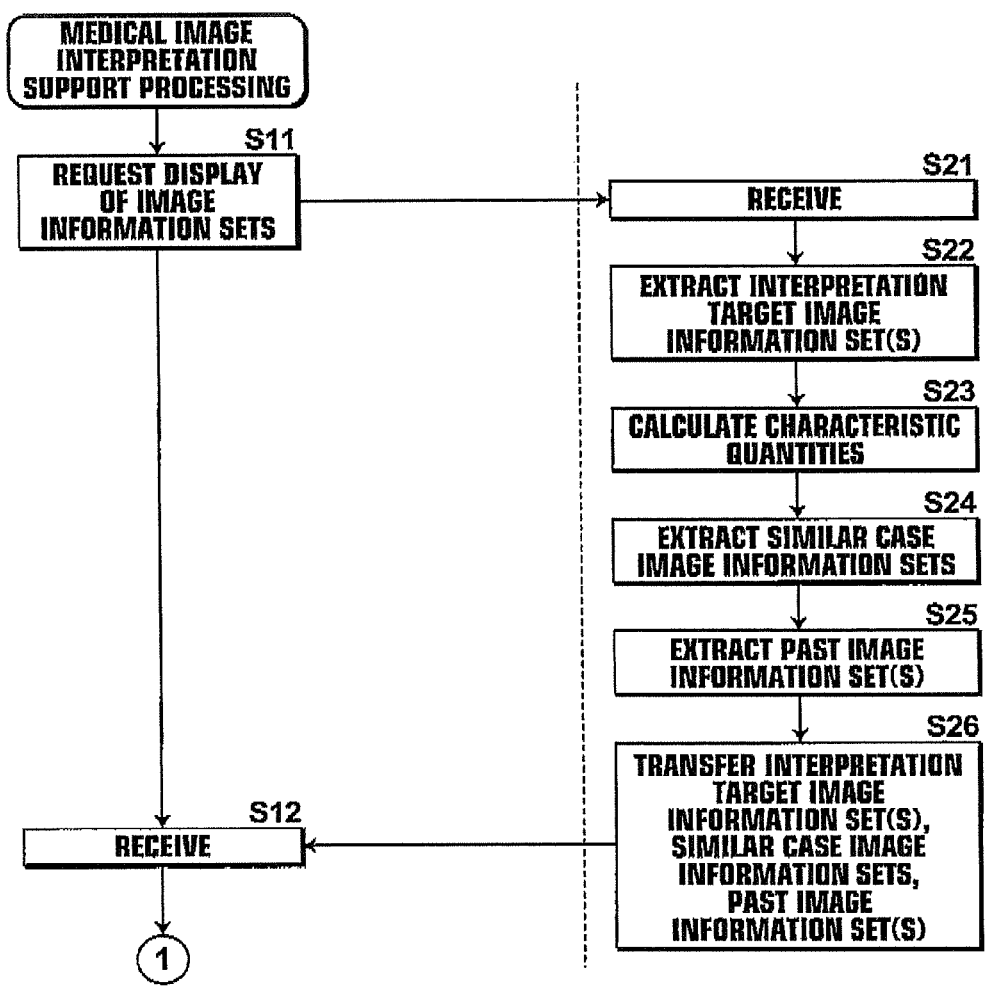
FIG. 5 is a flow chart showing procedures of medical image interpretation support processing (part 1)

Procedures of medical image interpretation support processing will be described next with reference to flow charts shown in FIGS. 5 and 6. The medical image interpretation support processing is carried out by the control unit 42 through readout of the medical image interpretation support program 431 from the storage unit 43 and execution thereof. In FIGS. 5 and 6, Steps S21 to S26 to the right of a broken line are carried out by the control unit 32 of the server 3 while Steps S31 to S33 to the right of a broken line are carried out by the control unit 92 of the server 9. FIGS. 7A, 7B, 8A, and 8B show examples of display on the monitor 45 at corresponding steps.

Figure 7A:
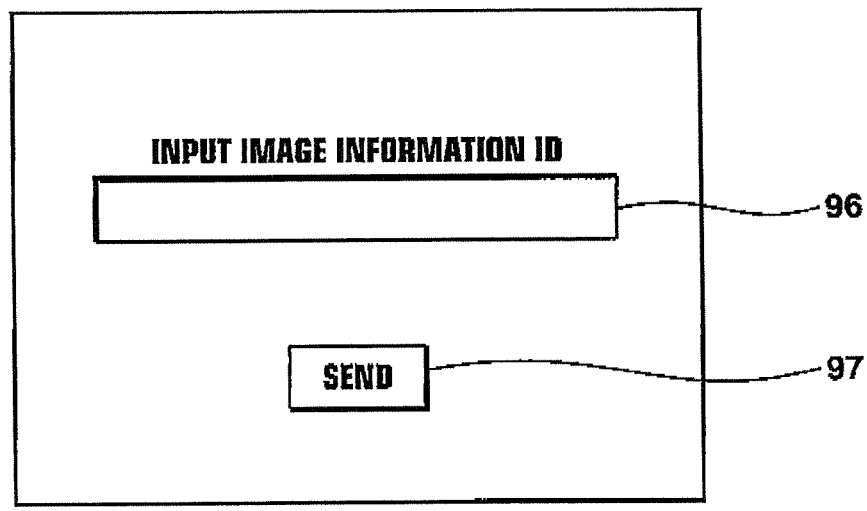
FIGS. 7A and 7B show examples of display on a monitor of the workstation for imaging diagnosis.
Figure 7B:
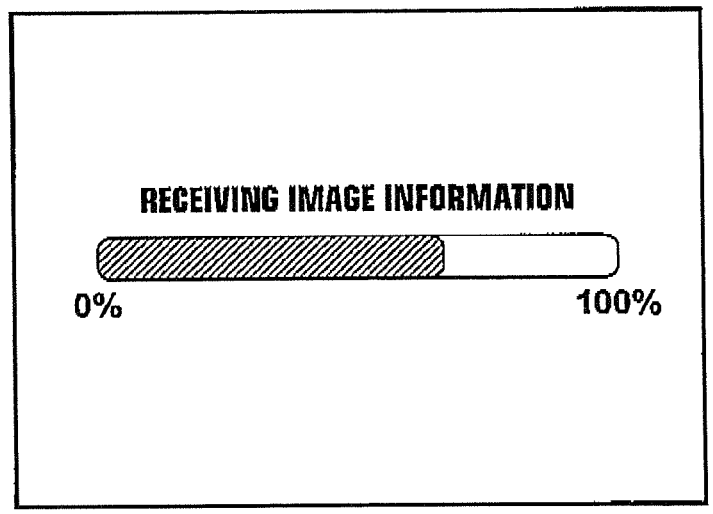

FIG. 7A shows an example of an initial screen when the medical image interpretation support processing is carried out. The radiologist inputs the identification number or the like of the interpretation target image information set or sets in an input box 96, and selects a Send button 97. In response, the control unit 42 causes the communication unit 44 to send the signal requesting transfer of the interpretation target image information set or sets to the server 3 (Step S11). FIG. 7B shows an example of display on the monitor 45 before completion of transfer of a signal of the requested interpretation target image information set or sets.

The communication unit 31 of the server 3 receives the signal requesting transfer of the interpretation target image information set or sets (Step S21). In response, the control unit 32 extracts the interpretation target image information set or sets from the medical information sets 81 in the medical image database 8 (Step S22). The characteristic quantity calculation unit 321 calculates the characteristic quantities in the region of interest in the image or images included in the interpretation target image information set or sets (Step S23).

The similar case search unit 322 searches the medical image database 8 for the corresponding medical image information sets 81 including the images whose similarity to the interpretation target image or images is 50% or more according to the characteristic quantities having been calculated, and extracts the image information sets (Step S24).

The past image search unit 323 searches the medical image database 8 for the past image information set or sets pertinent to the interpretation target image information set or sets according to the name of the patient included in the accompanying information of the interpretation target image information set or sets, and extracts the corresponding image information set or sets (Step S25). In the case where the patient as the subject of the interpretation target image or images has been diagnosed but has not been subjected to imaging, the medical image database 8 does not have the medical image information set or sets 81 as the past image information set or sets. In addition, depending on the search condition, the medical image database 8 may not have the medical image information set or sets 81 as the past image information set or sets, in the case where the patient has been imaged by the corresponding modality for the first time although he/she was imaged by another one of the modalities before or in the case where the body part of the patient has been imaged for the first time, for example. In such cases, the past image search unit 323 judges that the medical image information set or sets 81 as the past image information set or sets does/do not exist, and quits the search.

The control unit 32 causes the communication unit 31 to send the interpretation target image information set or sets, the similar case image information sets, and the past image information set or sets having been extracted (Step S26). At this time, the control unit 32 sends the similarity of the respective similar case images to the interpretation target image or images by adding the similarity to the corresponding similar case image information sets. The communication unit 44 of the imaging diagnosis workstation 4 receives the interpretation target image information set or sets, the similar case image information sets, and the past image information set or sets (Step S12). The first examination judgment unit 421 judges that the interpretation target image or images is/are a first examination image or first examination images if the past image information set or sets is/are not included in the information sets having been sent, and otherwise judges that the interpretation target image or images is/are not a first examination image or first examination images. In the case where the interpretation target image or images is/are a first examination image or first examination images (Step S13;YES), the display control unit 422 generates a display signal to display the interpretation target image or images on the monitor 45, and outputs the display signal to the monitor 45 (Step S14). The display control unit 422 further generates a display signal to display on the monitor 45 the similar case images whose similarity to the interpretation target image or images is 50% or more among the similar case images sent from the server 3, and outputs the display signal to the monitor 45 (Step S15).

Figure 8A:
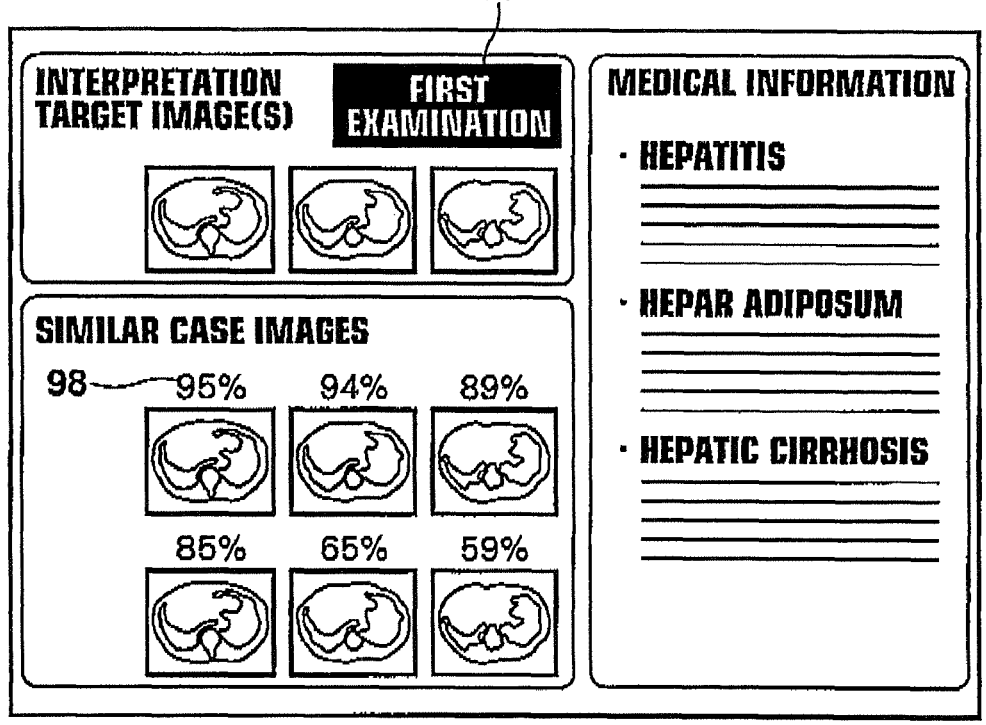
FIGS. 8A and 8B show examples of display on the monitor of the workstation for imaging diagnosis.

The control unit 42 reads out the imaged body part from the accompanying information included in the interpretation target image information set or sets having been transferred, and causes the communication unit 44 to send the body part as the search condition data to the server 9 (Step S16). The communication unit 91 of the server 9 receives the search condition data (Step S31), and the medical information search unit 93 searches the medical information database 10 for the medical information set or sets 101 corresponding to the search condition data, in order to extract the medical information set or sets 101 (Step S32). The control unit 92 causes the communication unit 91 to send the extracted medical information set or sets (Step S33). The communication unit 44 of the imaging diagnosis workstation 4 receives the medical information set or sets (Step S17). The display control unit 422 generates a display signal to display the medical information set or sets on the monitor 45, and outputs the display signal to the monitor 45 (Step S18). In this manner, the interpretation target image or images, the similar case images whose similarity to the interpretation target image or images is 50% or more, and the medical information set or sets are displayed on the monitor 45. An example of display on the monitor 45 is shown in FIG. 8A. At this time, the interpretation target image or images may be displayed together with characters or a mark (such as the mark indicated by "99" in FIG. 8A) representing that the interpretation target image or images is/are a first examination image or first examination images. The figures indicated by "98" in FIG. 8A represent the similarity to the interpretation target image or images. The control unit 42 then completes the medical image interpretation support processing.

Figure 8B:
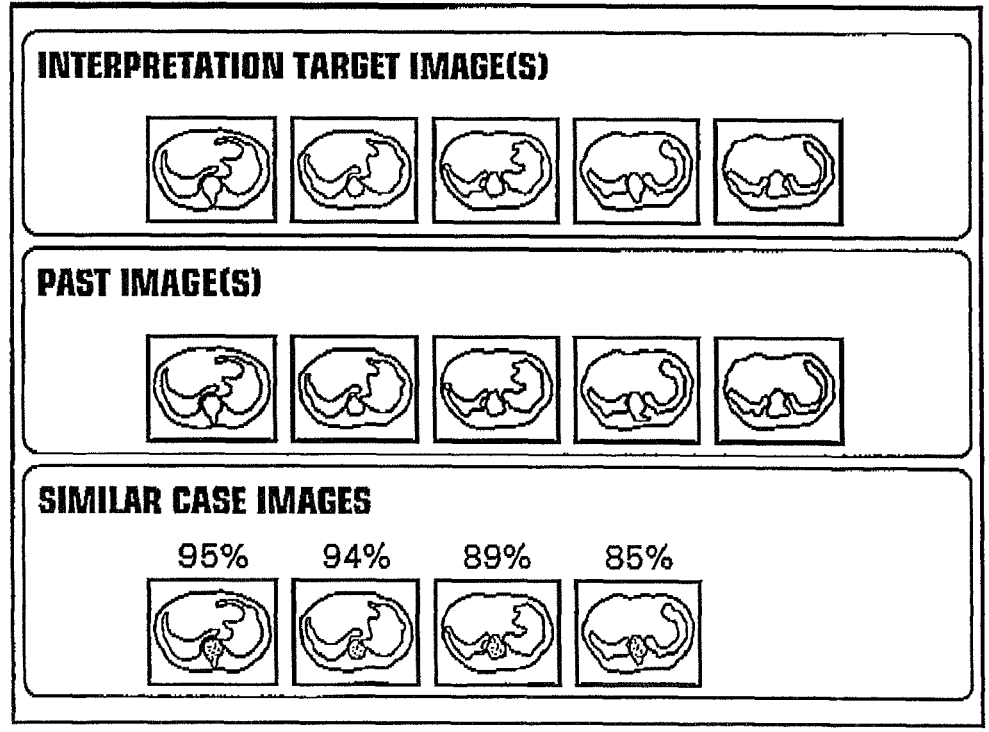

In the case where the interpretation target image or images is/are not a first examination image or first examination images (Step S13; NO), the display control unit 422 generates a display signal to display the past image or images on the monitor 45 together with the interpretation target image or images, and outputs the display signal to the monitor 45 (Step S19). The display control unit 422 further generates a display signal to display on the monitor 45 the similar case images whose similarity to the interpretation target image or images is 80% or more among the similar case images sent from the server 3, and outputs the display signal to the monitor 45 (Step S15). In this manner, the interpretation target image or images, the past image or images, and the similar case images whose similarity to the interpretation target image or images is 80% or more are displayed on the monitor 45. An example of display on the monitor 45 is shown in FIG. 8B. The control unit 42 then completes the medical image interpretation support processing.

As has been described above, a larger number of the similar case images are displayed together with the interpretation target image or images in the case where the interpretation target image or images is/are a first examination image or first examination images than in the case where the interpretation target image or images is/are not a first examination image or first examination images but an image or images obtained in a so-called follow-up examination, the similar case images can be displayed according to the number and progress of examinations. Consequently, the image information sets of appropriate content can be efficiently provided to the radiologist.

The similarity of the similar case images for the case where the interpretation target image or images is/are a first examination image or first examination images is smaller than the similarity thereof for the case where the interpretation target image or images is/are not a first examination image or first examination images in this embodiment so that more of the similar case images can be displayed than in the case where the interpretation target image or images is/are not a first examination image or first examination images. However, another method may be used for display of the similar case images.

For example, in the case where the interpretation target image or images is/are a first examination image or first examination images, the similar case images whose similarity is 50% or more may be displayed together with the interpretation target image or images so that the radiologist can select a portion of the displayed similar case images that seems to be useful for reference. In this case, link information to the selected similar case images is stored as a part of the accompanying information in the interpretation target image information set or sets. Upon revisit of the patient as the subject of the interpretation target image or images to the hospital or the like for further imaging, a medical image or medical images obtained newly is/are displayed as a new interpretation target image or new interpretation target images on the monitor 45 with the previous interpretation target image or images as the past image or images. At this time, the similar case images indicated by the link information stored in the accompanying information in the past image information set or sets (that is, the similar case images selected by the radiologist at the time of the previous visit) are also displayed. In this manner, only the similar case images selected by the radiologist as useful reference images are displayed in a follow-up examination, and the image information sets necessary for the radiologist can be immediately provided.

The functional units in the imaging diagnosis workstation 4 carry out the interpretation target image transfer request and the display control of the interpretation target image or images, the similar case images, and the past image or images. However, each of the image reference workstations 5a to 5c may have the same functions. In this case, the image reference workstations 5a to 5c are included in the medical image interpretation support system 200.

In the case where the interpretation target image or images is/are not a first examination image or first examination images, the past image or images is/are displayed together with the interpretation target image or images. However, only the interpretation target image or images may be displayed. In this case, the past image or images may further be displayed in response to a predetermined operation of the input unit 41.

The display control unit 422 carries out the display control of the interpretation target image or images, the similar case images, and the past image or images. However, the display control unit 422 may display the accompanying information 812 and the diagnosis information 81b together with the images. Alternatively, the accompanying information 812 and the diagnosis information 81b may be displayed or undisplayed according to a predetermined operation of the input unit 41.

The characteristic quantity calculation unit 321 automatically detects the region of interest in the interpretation target image or images. However, the radiologist may determine the region of interest therein by use of the imaging diagnosis workstation 4. In this case, only the interpretation target image information set or sets extracted at Step S22 is/are sent from the server 3 to the imaging diagnosis workstation 4, and the radiologist determines the region of interest while viewing the interpretation target image or images displayed on the monitor 45. Information related to the region of interest is sent to the server 3, and the characteristic quantity calculation unit 321 calculates the characteristic quantities (Step S23). The similar case image information sets are then extracted (Step S24).

Figure 9:
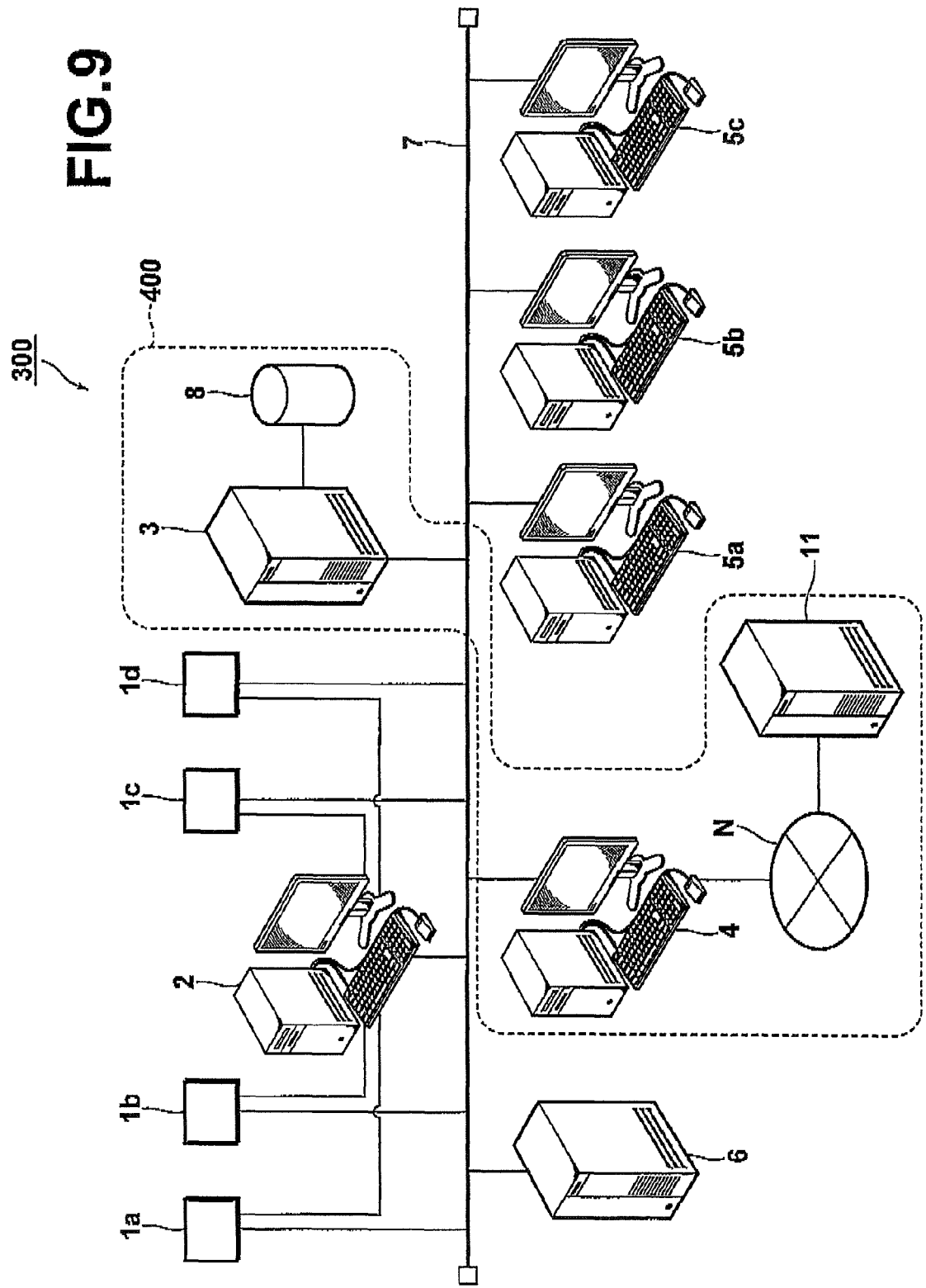
FIG. 9 shows the configuration of a network system having another medical image interpretation support system.

The medical information set or sets displayed on the monitor 45 of the imaging diagnosis workstation 4 is/are sent from the image information database 10 via the server 9. However, a WWW server or the like connected to a communication network such as the Internet may be used therefor. FIG. 9 shows the configuration of a network system 300 having a medical image interpretation support system 400 of as a modification of the embodiment of the present invention. In the network system 300 shown in FIG. 9, the same elements having the same functions as the network system 100 in FIG. 1 have the same reference codes, and will not be described below in detail. The medical image interpretation support system 400 comprises the imaging diagnosis workstation 4, the server 3, the medical image database 8, a communication network N, and a WWW server 11.

The imaging diagnosis workstation 4 and the WWW server 11 are connected to each other via the communication network N. The communication network N may be a communication network of any form such as a wide area network like the Internet, a public communication network, a dedicated network, or a mobile communication network. The WWW server 11 discloses a medical information site on the Internet. The medical information site is a site that discloses basic information of diseases and past issues of journals of medical information or academic papers, for example. By accessing the medical information site from a general purpose computer or the like for inputting a keyword in a search box to send the keyword, medical information corresponding to the keyword is displayed. Upon display of the interpretation target image or images, the imaging diagnosis workstation 4 sends the item of imaged body part or the like stored in the accompanying information in the interpretation target image information set or sets as a search keyword to the server 11, and causes the medical information site having a result of the search to be displayed on the monitor 45. In this manner, the medical information can be displayed easily without the medical information database 10 on the network 7.

What is claimed is:

1. A medical image interpretation support system comprising:
   storage means for storing image data sets obtained by imaging patients;
   similar case search means for extracting similar case image data sets representing similar case images having a characteristic similar to an interpretation target image or interpretation target images from the image data sets stored in the storage means; and
   display control means for controlling display of the interpretation target image or images and the similar case images on a monitor or monitors, the medical image interpretation support system further comprising:
   first examination judgment means for judging whether the interpretation target image or images is/are a first examination image/first examination images, wherein
   the display control means controls the display in such a manner that the number of the similar case images displayed together with the interpretation target image or images in the case where the first examination judgment means has judged that the interpretation target image or images is/are a first examination image or first examination images is larger than the number of the similar case images displayed together with the interpretation target image or images in the case where the first examination judgment means has judged that the interpretation target image or images is/are not a first examination image or first examination images.

2. The medical image interpretation support system according to claim 1, further comprising medical information search means for extracting medical information, wherein
   the display control means controls the display to further display the medical information extracted by the medical information search means in the case where the first examination judgment means has judged that the interpretation target image or images is/are a first examination image or first examination images.

3. The medical image interpretation support system according to claim 1, further comprising past image search means for extracting at least one past image data set representing a past image or past images obtained in the past regarding the same patient as the interpretation target image or images from the image data sets stored in the storage means, wherein
   the display control means controls the display to further display the past image or images extracted by the past image search means in the case where the first examination judgment means has judged that the interpretation target image or images is/are not a first examination image or first examination images.

4. The medical image interpretation support system according to claim 3 wherein the first examination judgment means judges that the interpretation target image or images is/are a first examination image or first examination images in the case where the past image search means cannot extract the past image data set or sets.

5. The medical image interpretation support system according to claim 3, wherein the past image search means extracts the past image data set or sets of the patient including the same body part as the interpretation target image or images.

6. The medical image interpretation support system according to claim 1, further comprising electronic chart storage means for storing electronic charts including history information of examinations involving imaging, wherein
   the first examination judgment means judges whether the interpretation target image or images is/are a first examination image/first examination images by referring to the history information included in a corresponding one of the electronic charts to the patient of the interpretation target image or images stored in the electronic chart storage means.

7. A medical image interpretation support method comprising the steps of:
   extracting similar case image data sets representing similar case images having a characteristic similar to an interpretation target image or interpretation target images from image data sets obtained by imaging patients and stored in storage means; and
   displaying the interpretation target image or images and the similar case images on a monitor or monitors, wherein the step of displaying comprises the steps of:
   judging whether the interpretation target image or images is/are a first examination image/first examination images; and
   displaying the similar case images together with the interpretation target image or images in such a manner that the number of the similar case images displayed together with the interpretation target image or images in the case where the interpretation target image or images has/have been judged to be a first examination image or first examination images is larger than the number of the similar case images displayed together with the interpretation target image or images in the case where the interpretation target image or images has/have been judged to be not a first examination image or first examination images in the step of judging.

8. A recording medium storing a medical image interpretation support program causing a computer to execute procedures of first examination judgment and display control, the computer comprising a medical image interpretation support system including:
   storage means for storing image data sets obtained by imaging patients;
   similar case search means for extracting similar case image data sets representing similar case images having a characteristic similar to an interpretation target image or interpretation target images from the image data sets stored in the storage means; and display control means for controlling display of the interpretation target image or images and the similar case images on a monitor or monitors, the computer having the display control means and caused to execute:

the first examination judgment procedure for judging whether the interpretation target image or images is/are a first examination image/first examination images; and the display control procedure for controlling the display in such a manner that the number of the similar case images displayed together with the interpretation target image or images in the case where the interpretation target image or images has/have been judged to be a first examination image or first examination images in the first examination judgment procedure is larger than the number of the similar case images displayed together with the interpretation target image or images in the case where the interpretation target image or images has/have been judged to be not a first examination image or first examination images in the first examination judgment procedure.

* * * * *